United States Patent [19]

Miraki

[11] Patent Number: 5,387,226
[45] Date of Patent: Feb. 7, 1995

[54] RAPID EXCHANGE CATHETER

[75] Inventor: Manouchehr Miraki, Aliso Viejo, Calif.

[73] Assignee: Baxter International Inc., Deerfield, Ill.

[21] Appl. No.: 181,686

[22] Filed: Jan. 14, 1994

[51] Int. Cl.⁶ .............................................. A61M 29/00
[52] U.S. Cl. ...................................... 606/194; 604/96
[58] Field of Search ........................ 606/191, 192, 194; 604/95-104

[56] References Cited

U.S. PATENT DOCUMENTS

| | | |
|---|---|---|
| 4,748,982 | 6/1988 | Horzewski et al. . |
| 4,762,129 | 8/1988 | Bonzel . |
| 4,771,777 | 9/1988 | Horzewski et al. . |
| 4,824,435 | 4/1989 | Giesy et al. . |
| 4,928,693 | 5/1990 | Goodin et al. . |
| 4,932,413 | 6/1990 | Shockey et al. . |
| 4,947,864 | 8/1990 | Shockey et al. . |
| 4,988,356 | 1/1991 | Crittenden et al. ................ 606/194 |
| 5,061,273 | 10/1991 | Yock et al. . |
| 5,106,363 | 4/1992 | Nobuyoshi et al. . |
| 5,135,535 | 8/1992 | Kramer ................ 606/194 |
| 5,154,725 | 10/1992 | Leopold ................ 606/194 |

OTHER PUBLICATIONS

Technical Article, *Gull-wing haptic design for posterior chamber intraocular lens*, Samuel Masket, M.D.

*Primary Examiner*—Stephen C. Pellegrino
*Assistant Examiner*—William W. Lewis
*Attorney, Agent, or Firm*—Poms Smith Lande & Rose

[57] ABSTRACT

A balloon dilatation catheter of the mono-rail type includes a distal mono-rail section traversing a dilatation balloon of the catheter, and a sheath member slidably movable axially of the remainder of the catheter and having a sheath section receiving an axial portion of the guide wire to in a first position effectively increase the mono-rail length of the catheter, and in a second position reduce the mono-rail length of the catheter to the length of the mono-rail section.

20 Claims, 2 Drawing Sheets

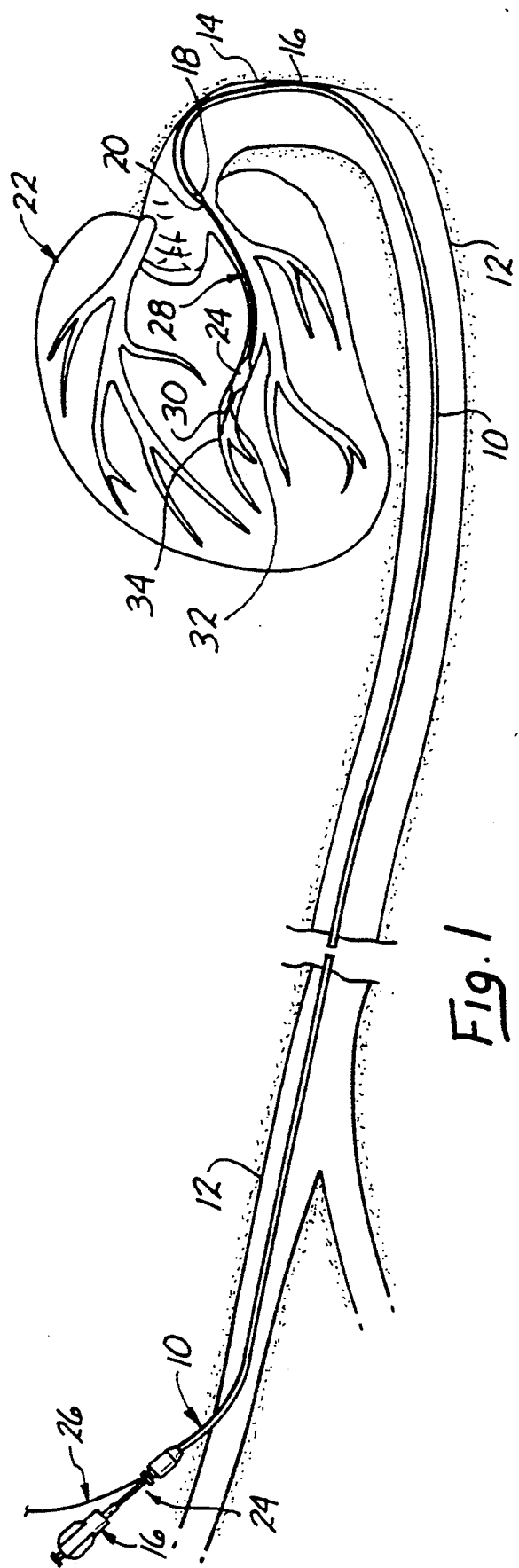
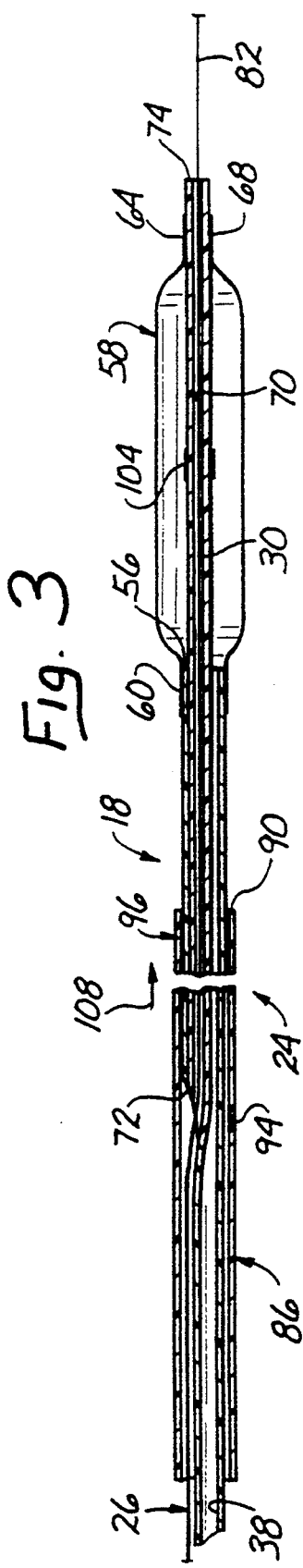

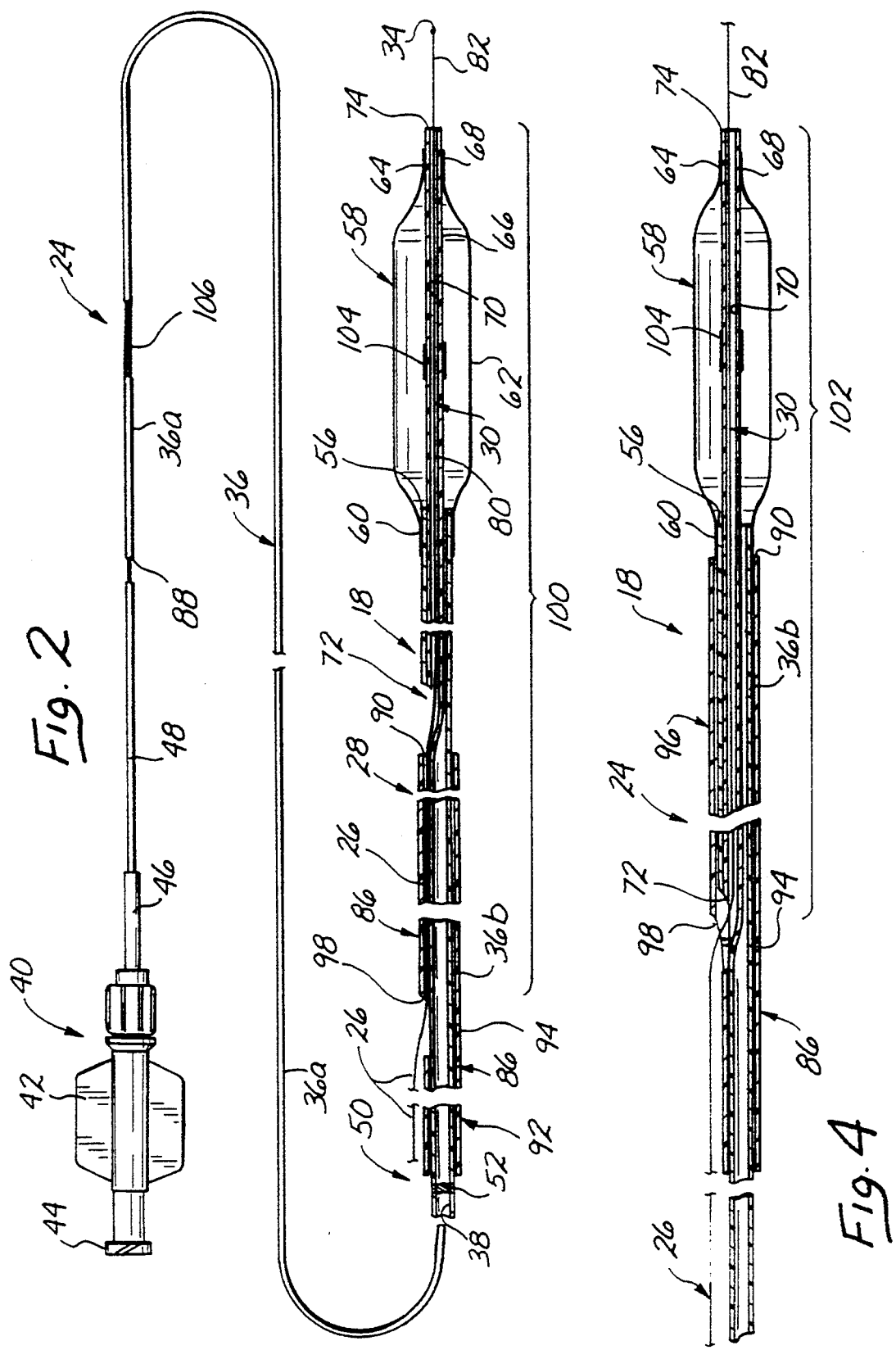

he present invention is in the field of balloon dilatation catheters used for cardiac angioplasty. More particularly, the present invention is in the field of balloon dilatation catheters of the so-called mono-rail configuration.

RAPID EXCHANGE CATHETER

BACKGROUND OF THE INVENTION

1. Field of the Invention

The present invention is in the field of balloon dilatation catheters used for cardiac angioplasty. More particularly, the present invention is in the field of balloon dilatation catheters of the so-called mono-rail configuration.

2. Related Technology

Therapeutic balloon dilatation catheters are known in the art which are of the so-called "mono-rail" configuration. Such monorail catheters generally have only a comparatively short distal mono-rail portion of the catheter which is slidably received over a guide wire. Other than the comparatively short distal portion of the guide wire which is received within the catheter, the remainder of the guide wire is exposed externally of the catheter. During angioplasty, a guide catheter is generally inserted into a patient and serves both to guide a therapeutic catheter along the vascular pathway to a location close to the heart, and to protect the patient's vessels from trauma which could be caused by contact from the therapeutic catheter.

However, this guide catheter provides a pathway only part of the way to the patient's heart. Beyond the distal end of the guide catheter, the therapeutic catheter generally extends unprotected within the vascular system of the patient. A guide wire is used to guide the therapeutic catheter the remainder of the distance to the location of treatment. With a mono-rail configuration of catheter, because the guide wire is exposed externally of the therapeutic catheter with the exception of the comparatively short mono-rail distal portion, the therapeutic catheter may be pulled back while leaving the guide wire in place, and without the need to use an extension for the guide wire. Because the guide catheter and guide wire both are left in place within the patient when the therapeutic catheter is withdrawn, a second therapeutic catheter of different size or type, for example, can easily retrace the path back to the location of treatment.

Unfortunately, the mono-rail type of catheters generally expose a section of the guide wire proximally of the distal mono-rail portion of the catheter and distally of the distal end of the guide catheter. The remainder of the guide wire is exposed. That is, only a portion of the guide wire is sheathed and slidably received in the distal end mono-rail portion of the therapeutic catheter, and the therapeutic catheter may be advanced beyond the end of the guide catheter sufficiently that a length of the guide wire is exposed. This exposed portion of guide wire can cause undesirable and detrimental local trauma to the patient's vascular system.

A conventional single-lumen mono-rail type of therapeutic catheter is known in accord with U.S. Pat. No. 4,762,129, issued 9 Aug. 1988, to T. Bonzel. The teaching of the Bonzel patent appears to be to configure a mono-rail catheter of the disclosed type with a comparatively short guide lumen which traverses the dilatation balloon of the catheter. The guide lumen is defined by a short section of flexible tubing. This section of tubing which traverses the dilatation balloon to provide a passage for the guide wire is about equal in length to the dilatation balloon itself. Proximally of the distal guide lumen of this catheter, the guide wire is exposed externally of the therapeutic catheter.

Another conventional therapeutic catheter of the mono-rail type is known in accord with U.S. Pat. No. 5,061,273, issued 29 Oct. 1991, to P. Yock. According to the teaching of the Yock patent, a mono-rail type of therapeutic catheter may be made with a comparatively long or extended distal mono-rail portion. However, the ease of catheter exchange which is the underlying principle for the mono-rail configuration of catheter is compromised by the extended length of the mono-rail portion of the catheter.

Yet another conventional mono-rail type of therapeutic catheter is seen in U.S. Pat. No. 4,748,982, issued 7 Jun. 1988 to M. J. Horzewski, et al. The teaching of the Horzewski patent appears to be to make a mono-rail type of catheter with a distal end mono-rail section which in the use position of the guide wire is sufficiently long so as to protect the patient from guide wire trauma. In order to still allow exchange of the therapeutic catheter while leaving the guide wire in place without the need for a guide wire extension, the Horzewski patent teaches to provide the distal end mono-rail section with a slit extending distally from a notch out of which the proximal portion of the guide wire extends from this mono-rail section. This slit extends distally almost to the dilatation balloon. When the guide wire is moved distally along this slit to a withdrawal position, the length of the mono-rail distal section of the therapeutic catheter is effectively shortened.

That is, with the catheter taught by the Horzewski patent, in order to facilitate withdrawal of the therapeutic catheter, this therapeutic catheter is withdrawn through the guide catheter until the notch is exposed externally of the patient. Thereafter, the guide wire must be forced to pass distally along the slit to a location adjacent to the dilatation balloon as the therapeutic catheter is further withdrawn, and without withdrawing the guide wire. In order to complete removal of the therapeutic catheter, the distal portion of this catheter must then be slid along the proximal part of the guide wire still without displacing the guide wire distal end from its preferred location within the patient across the treatment site. These two stages of catheter removal can be rather difficult because the guide wire is grasped frictionally in the slit of the catheter. Understandably, to accomplish this catheter removal without displacing the distal end of the guide wire is a process which requires considerable skill and care. In the event the guide wire distal end is inadvertently displaced from its desired position within the patient, then the route back to the treatment site is partially lost and must be reestablished by manipulation of the guide wire. Additional vascular trauma and risk to the patient can result from such manipulation of the guide wire to reestablish its desired position.

SUMMARY OF THE INVENTION

In view of the deficiencies of conventional technology, it is an object for the present invention to provide a mono-rail configuration of balloon dilatation therapeutic catheter which effectively includes a mono-rail portion of variable length, and which is free of a guide wire slit which can frictionally and undesirably grasp the guide wire during catheter withdrawal.

An additional object for the present invention is to provide such a therapeutic catheter with an axially movably mono-rail guide wire sheath which at a distal end portion thereof includes a sleeve portion in a first position sheathing the guide wire to effectively lengthen the mono-rail portion of the catheter.

Still another object of the present invention is to provide such a therapeutic catheter in which the guide wire sheath element may move axially in the distal direction to a second position overlying a part of the mono-rail guide portion of the therapeutic catheter proximal of the dilatation balloon, effectively shortening the mono-rail portion of the catheter.

Yet another object of the present invention is to provide a method of treatment in which a mono-rail configuration of catheter is used in a use configuration having an elongate mono-rail length to protect the patient from vascular trauma caused by contact of the guide wire with the vascular system, and is changed to a withdrawal configuration with a shortened mono-rail length for withdrawal of the catheter from the patient preparatory to catheter exchange.

Accordingly, the present invention provides an elongate balloon dilatation catheter having a distal mono-rail guide section, a dilatation balloon, and a mono-rail sheath member slidably movable axially along a shaft portion of the catheter between a first position sheathing the guide wire and effectively increasing the mono-rail length of the catheter, in a second position of the mono-rail sheath member the mono-rail length of the catheter substantially being defined only by the mono-rail guide section.

These and other objects and advantages of the present invention will be apparent from a reading of the following detailed description of a single exemplary preferred embodiment of the present invention, taken in conjunction with the following drawing Figures, in which like reference numerals designate the same feature, or features equivalent in structure or function.

DESCRIPTION OF THE DRAWING FIGURES

FIG. 1 schematically presents a representation of a guide catheter which is introduced into a patient's femoral artery and which extends at its distal end around the aortic arch to terminate at a location adjacent to the patient's heart. A therapeutic catheter extends through the guide catheter to the patient's heart.

FIG. 2 provides a plan view of a therapeutic catheter embodying the present invention in a use configuration, and in which the foreground portion of the Figure is drawn at a larger scale than the background portion in order to better illustrate salient features of the invention;

FIG. 3 provides a fragmentary view similar to the foreground portion of FIG. 2, and depicting the therapeutic catheter in transition between its use configuration and its withdrawal configuration; and FIG. 4 is a fragmentary view similar to the foreground portion of FIG. 2, and depicting the therapeutic catheter in an alternative or withdrawal configuration.

DETAILED DESCRIPTION OF THE PREFERRED EMBODIMENT

Considering first FIGS. 1 and 2 together, a schematic representation is provided of a tubular guide catheter 10 introduced into a patient's femoral artery 12, and extending upwardly to terminate at the aortic arch 14. The guide catheter 10 includes a distal recurve section 16 which provides for a distal end 18 of the guide catheter 10 to dispose an end opening 20 of the tubular guide catheter 10 toward the patient's heart 22. A therapeutic balloon dilatation catheter 24 is introduced into the guide catheter 10 along with a guide wire assembly 26. From the opening 20 of the guide catheter 10, a distal end portion 28 of the therapeutic catheter 24 extends to the patient's heart 22. This distal end portion 28 is slidably received over a distal portion 30 of the guide wire assembly 26, which is seen projecting distally from an open end 32 of the therapeutic catheter 24. This guide wire assembly 26 at the distal portion 30 includes a radiopaque tip part 34 by which a physician can visualize the guide wire location and steer the guide wire assembly 26 and therapeutic catheter 24 to a treatment site for the patient.

Viewing now FIG. 2, the therapeutic balloon dilatation catheter 24 is shown in a use configuration. The catheter 24 includes an elongate catheter shaft portion 36 which is flexible, but which has good pushability and steerability because a proximal part 36a of the shaft is made of hypotube. That is, the shaft portion 36a is formed of small diameter metallic tubing having a wall thickness which is comparatively thin. As an example only, the tubing from which the shaft portion 36a is fabricated may have an outer diameter of about 0.023 inches, and a wall thickness of 0.0025 inches. Consequently, the shaft portion 36a has an internal passage or lumen 38 of about 0.018 inches diameter. This internal passage is best seen in the foreground portion of FIG. 1.

At a proximal end portion 40, the catheter 24 includes a coupling member 42, which is sealingly joined to the shaft portion 36a, and which defines a luer type of fitting 44. The luer fitting 44 communicates with the passage 38 of the shaft 36. Also, the proximal end portion 40 may also include one or more reinforcing sleeves 46, 48 extending distally from the coupling member 42.

At a location indicated by the arrow 50 along the length of the shaft 36, the metallic shaft portion 36a is joined in end-to-end relation with and forms a butt joint bond 52 with a flexible polymeric tubular part 36b of the shaft 36. The polymeric tubular part 36b is similar in diameter and wall thickness with the metallic part 36a, but is considerably more flexible. This polymeric tubular portion 36b of the shaft 36 defines the distal end portion for the catheter 24, as has been indicated with the numeral 28.

This catheter shaft portion 36b defines a distal end 56, which is spaced proximally of the distal end of the balloon catheter assembly 24, as will be further explained, and at which an expansible dilatation balloon 58 is secured to the shaft portion 36b by means of a bond 60. This dilatation balloon 58 includes a side wall 62 and a distal end part 64 which is similarly bonded to a comparatively smaller tubular member 66 at a bond 68. The tubular member 66 defines an internal passage 70 opening distally, and extends proximally in the balloon 58 and in the catheter shaft distal end portion 18 to a port 72. That is, the tubular member 66 is joined with the polymeric portion 36b of the catheter shaft 36 so that the passage 70 of this member opens outwardly on the portion 36b to define the port 72. It will be noted that the port 72 extends or is angulated toward the proximal end of the catheter 24. At its distal end 74, the tubular member 66 defines a corresponding distal end for the catheter 24.

In order to guide the catheter 24 along a vascular pathway, the passage 70 accepts and slidably passes the distal end portion 30 of the guide wire assembly 26. In other words, the passage 70 defines a mono-rail guide portion of the catheter 24 whereat the latter is slidably guided along the guide wire assembly 26. This guide wire assembly 26 includes an elongate shaft portion 80 which is generally wire-like. Distal end portion 30 of the guide wire assembly 26, in contrast, includes a spring-like portion 82 which is exceedingly flexible, but which may be preformed with a curve or bend for example, to help in steering the guide wire assembly 26 along a selected vascular pathway. The distal end portion 30 terminates in and carries the radiopaque tip member 34 to assist a physician in visualizing the location of the guide wire assembly 26 by use of a fluoroscope. It will be noted that proximally of the port 72, the guide wire assembly 26 is exposed externally of the catheter shaft 36.

In order to effectively extend the mono-rail portion of the catheter 24 beyond the length of the passage 70, a tubular mono-rail sheath member 86 is slidably carried on the outside of the shaft 36 between the sleeves 46, 48, and the balloon member 58. That is, the sheath member 86 includes a proximal end 88 which may abut one of the sleeves 46, 48 to define a limit of axial movement of the sheath member 86 in the proximal direction. Also, the sheath member 86 includes a distal end 90 which may abut the bond 60 to define a limit of axial movement of the sheath member 86 in the distal direction. More particularly, the sheath member 86 includes a proximal section 92, which has an inner diameter just sufficiently large enough so as to be slidably received over the shaft 36 of the catheter 24. At a bond 94, the proximal section 92 is joined with a distal section 96 having an inner diameter sufficiently larger that the outer diameter of the shaft 36 that the guide wire assembly 26 may also be received in this section of the sheath member 86. At the bond 94, the sheath member 86 defines a port 98 through which extends the guide wire assembly 26.

As is seen in FIG. 2, in a use configuration of the catheter 24 with the guide wire sheath member 86 withdrawn to its limit of axial movement in the proximal direction, the distal end 90 of the sheath member 86 is disposed just proximally of the port 72. Consequently, the guide wire assembly 26 is concealed within the monorail passage 70 of the catheter 24, and also within the section 96 of the sheath member. As so configured, the catheter 24 has a mono-rail length generally indicated with the numeral 100 and protects the patient from trauma caused by contact by the guide wire assembly 26. That is, the distal portions of the catheter 24 which may be exposed outside of the guide catheter 10 as seen in FIG. 1 have the guide wire assembly 26 sheathed or concealed within them. Consequently, the patient cannot be injured by the guide wire assembly 26.

In order to withdraw the catheter 24 (possibly to facilitate exchange of the catheter 24 with a different treatment catheter while leaving the guide wire assembly 26 in place for the replacement catheter to retrace the path back to the treatment site), the catheter 24 is first withdrawn in its use configuration of FIG. 2 until the distal end 74 is within the guide catheter 10. During this initial phase of withdrawal of the catheter 24, simple manual holding of a proximal end portion of the guide wire assembly 26 stationary will prevent the guide wire assembly from being dragged out of its established position across the treatment site. Next, as is depicted in FIG. 3 with arrow 108, the sheath member 86 is advanced distally to its withdrawal position seen in FIG. 4. This advancement of the sheath member 86 is accomplished by manually grasping of the proximal portions of the shaft 36a (at the coupling member 42, for example) and of the sheath member 86 (adjacent to the proximal end 88 thereof, for example), and moving the sheath member 86 distally relative to the shaft 36 while holding the latter stationary. While the balloon 58 is illustrate in an inflated condition in FIG. 4 for ease of illustration, it will be understood that the balloon 58 would ordinarily be deflated during all phases of withdrawal of the catheter 24. In this withdrawal configuration of the catheter 24, the sheath member 86 generally aligns port 72 with port 98. Consequently, the catheter 24 has a mono-rail length in its withdrawal configuration which is indicated by the numeral 102 in FIG. 4. It will be noted that the mono-rail length 100 of the catheter 24 in its use configuration is considerably greater, and may in fact be about twice the mono-rail length 102 in its withdrawal configuration of the catheter 24, as seen in FIG. 2.

In order to further assist a physician in visualizing the position of the balloon 58 within a patient, a radiopaque marker 104 may be carried on the tubular member 66 centered in the balloon 58. Also, a mark may be provided at 106 which appears proximally of the proximal end 88 of the sheath member 86 when the latter is advanced distally fully to its second position as seen in FIG. 4 to configure the catheter 24 for withdrawal.

While the present invention has been depicted, described, and is defined by reference to a particularly preferred embodiment of the invention, such reference does not imply a limitation on the invention, and no such limitation is to be inferred. The invention is capable of considerable modification, alteration, and equivalents in form and function, as will occur to those ordinarily skilled in the pertinent arts. The depicted and described preferred embodiment of the invention is exemplary only, and is not exhaustive of the scope of the invention. Consequently, the invention is intended to be limited only by the spirit and scope of the appended claims, giving full cognizance to equivalents in all respects.

I claim:

1. An elongate balloon dilatation catheter comprising:

a shaft portion having a proximal end and a distal end;

a mono-rail guide section adjacent said distal end of said shaft portion, said mono-rail guide section including an axial passage communicating with a guidewire port through which an elongate guide wire may pass to be exposed outwardly of said catheter proximally of said mono-rail guide section, said axial passage defining a mono-rail length for said catheter;

an expansible dilatation balloon positioned about said mono-rail guide section; and a mono-rail sheath member slidably movable axially along said shaft portion proximal of said dilatation balloon, said sheath member comprising a proximal end, a distal end, and a guidewire port positioned between said proximal and distal ends;

wherein said sheath member is slidably movable along said shaft portion between a first position sheathing the guide wire proximally of said mono-rail guide section and cooperating therewith to effectively increase the mono-rail length of the catheter and a second position in which said sheath member port is aligned with said guidewire port of said shaft portion to allow the guidewire to be exposed outwardly of said catheter and said sheath member proximally of said aligned ports.

2. The dilatation catheter of claim 1 wherein said mono-rail sheath member is tubular in configuration.

3. The dilatation catheter of claim 2 wherein said sheath member includes a distal section of comparatively larger inner diameter opening at said distal end to receive in said first position of said sheath member both said catheter shaft and said guide wire in said distal section proximally of said axial passage.

4. The dilatation balloon of claim 3 wherein said sheath member distal section is receivable over a portion of said mono-rail length defined by said axial passage in said second position of said sheath member to substantially align said sheath member port with a proximal end of said axial passage and expose said guide wire outwardly of said catheter and proximally of said sheath member port.

5. The dilatation balloon of claim 4 wherein said sheath member includes a proximal section of comparatively smaller diameter which is slidably received on said catheter shaft portion.

6. The dilatation catheter of claim 1 wherein said catheter shaft portion comprises a proximal section of flexible metallic tubing.

7. The dilatation catheter of claim 6 wherein said catheter shaft portion also includes a distal section of polymeric tubing which is more flexible than said metallic tubing.

8. The dilatation catheter of claim 7 wherein said proximal metallic shaft section and said polymeric distal shaft section cooperatively define a butt joint therebetween.

9. The dilatation catheter of claim 1 wherein said sheath member in said second position thereof is slidably received over a portion of said monorail length of said catheter.

10. The dilatation catheter of claim 1, wherein said mono-rail length of the catheter is substantially defined only by said mono-rail guide section when said sheath member is in said second position.

11. A medical treatment catheter comprising:
  an elongate shaft portion, said elongate shaft portion including a proximal section of metallic tubing which at a proximal end thereof includes means for receiving pressurized inflation fluid, said proximal metallic shaft section at a distal end thereof joining in end-to-end fluid-communicating relation with a distal section of flexible polymeric tubing, said distal section adjacent to a distal end thereof sealingly joining in fluid communication with a dilatation balloon at a proximal bond for said balloon, said dilatation balloon at a distal bond thereof sealingly joining with a tubular member opening distally and extending proximally within both said balloon and a distal portion of said distal polymeric section to at a proximal end thereof sealingly join with said polymeric distal section and to open outwardly thereon to define a guide wire port angulated toward said proximal section of said catheter, said tubular member between said guide wire port and said distal opening thereof defining a mono-rail length for said catheter within which a guide wire may be sheathed; and
  a tubular sheath member slidably received axially over said proximal and distal sections and including a distal sheath section receiving therein said guide wire and defining a guide wire port spaced from a distal end of said sheath member and out of which said guide wire passes to be exposed proximally of said sheath member distal section, whereby in a first use position of said sheath member with said distal sheath section disposed proximally of said tubular member guide wire port the mono-rail length of said catheter is effectively extended by the length of said distal sheath section, and in a second withdrawal position of said sheath member in which said sheath member port is aligned with said guide wire port of said elongate shaft portion to allow said guide wire to be exposed outwardly of said catheter and said sheath member proximally of said aligned ports.

12. The catheter of claim 11 further including a reference mark on said catheter shaft with which a distal end of said sheath member aligns in said second withdrawal position of said sheath member.

13. The catheter of claim 11 wherein said proximal metallic catheter section is formed of hypotube.

14. The catheter of claim 13 wherein said hypotube has an outer diameter of substantially 0.023 inches, and a wall thickness of substantially 0.0025 inches.

15. The dilatation catheter of claim 11, wherein said mono-rail length of said catheter is defined substantially entirely by said tubular member.

16. An elongate medical balloon dilatation catheter comprising an elongate shaft portion at a distal end portion carrying an expansible dilatation balloon and at a proximal portion including means for receiving and discharging pressurized inflation fluid communicating with said dilatation balloon to expand and contract the latter; a tubular member within a distal section of said catheter traversing said dilatation balloon and opening both distally and proximally to slidably receive a guide wire therethrough, said tubular member defining a mono-rail length for said catheter, and a sheath member slidably received axially over said catheter shaft proximally of said balloon and including a distal section within which said guide wire is received, said sheath member including a port at a proximal end of said sheath member distal section through which said guide wire passes outwardly to be exposed outwardly of said catheter proximally of said tubular member and sheath member distal section.

17. The dilatation catheter of claim 16, wherein said catheter shaft portion comprises a guidewire port communicating with said tubular member, and wherein in said second position, said sheath member port is aligned with said guidewire port of said catheter shaft portion to allow the guidewire to be exposed outwardly of said catheter and said sheath member proximally of said aligned ports.

18. An elongate balloon dilatation catheter comprising:
  an elongate shaft portion having a proximal end and a distal end;
  a mono-rail guide section adjacent said distal end of said shaft portion, said mono-rail guide section including an axial passage through which an elongate guide wire may pass to be exposed outwardly of said catheter proximally of said mono-rail guide section, said axial passage defining a mono-rail length for said catheter;
  an expansible dilatation balloon positioned about said mono-rail guide section; and
  a sheath member slidably movable axially along said shaft portion proximal of said dilatation balloon, said sheath member comprising a proximal end, a distal end, and a guidewire port positioned between said proximal and distal ends;

wherein said sheath member is slidably movable axially along said shaft portion of said catheter between a first position sheathing the guide wire proximally of said distal mono-rail guide section and cooperating therewith to effectively increase the mono-rail length of the catheter and a second position in which the mono-rail length of the catheter is substantially defined only by said mono-rail guide section.

19. The dilatation catheter of claim 18, wherein said catheter shaft portion comprises a guidewire port communicating with said axial passage, and wherein in said second position, said sheath member port is aligned with said guidewire port of said shaft portion to allow the guidewire to be exposed outwardly of said catheter and said sheath member proximally of said aligned ports.

20. A method of exchanging catheters during a medical procedure, said method including the steps of:

(a) providing a first elongate catheter comprising a shaft portion, a distal mono-rail guide section defining a mono-rail length for said first catheter, and a guidewire port proximal to said mono-rail guide section;

(b) providing a tubular sheath member axially movable on said shaft portion of said first catheter and comprising a guidewire port;

(c) inserting said first catheter into a patient's vessel;

(d) sliding said sheath member to a first position sheathing said guide wire proximally of said mono-rail guide section to effectively lengthen said mono-rail length of said first catheter;

(e) sliding said sheath member proximally along said shaft portion of said first catheter to a second position in which said sheath member port is aligned with said guidewire port of said shaft portion to allow said guidewire to be exposed outwardly of said first catheter and said sheath member proximally of said aligned ports;

(f) removing said first catheter from said patient vessel; and (g) inserting a second elongate catheter into said patient vessel.

* * * * *